(12) United States Patent
Kim et al.

(10) Patent No.: US 11,298,560 B2
(45) Date of Patent: Apr. 12, 2022

(54) LIGHT OUTPUT DEVICE FOR CARING FOR USER USING ARTIFICIAL INTELLIGENCE AND METHOD OF OPERATING THE SAME

(71) Applicant: LG ELECTRONICS INC., Seoul (KR)

(72) Inventors: Hyoeun Kim, Seoul (KR); Jaehong Kim, Seoul (KR); Hangil Jeong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 206 days.

(21) Appl. No.: 16/539,705

(22) Filed: Aug. 13, 2019

(65) Prior Publication Data
US 2019/0366119 A1 Dec. 5, 2019

(30) Foreign Application Priority Data

Jul. 11, 2019 (KR) .......................... 10-2019-0083590

(51) Int. Cl.
*A61N 5/00* (2006.01)
*A61N 5/06* (2006.01)
(Continued)

(52) U.S. Cl.
CPC ............ *A61N 5/0616* (2013.01); *A61B 5/442* (2013.01); *A61B 5/443* (2013.01); *A61B 5/7267* (2013.01);
(Continued)

(58) Field of Classification Search
CPC ....... A61B 5/442; A61B 5/443; A61B 5/4836; A61B 5/7264; A61B 5/7267;
(Continued)

(56) References Cited

U.S. PATENT DOCUMENTS

2007/0064979 A1* 3/2007 Chhibber ............. G06K 9/2018
   382/118
2009/0245603 A1* 10/2009 Koruga .................. A61B 5/445
   382/128

(Continued)

FOREIGN PATENT DOCUMENTS

CN 107945173 A * 4/2018
KR 20140136590 A * 12/2014
(Continued)

OTHER PUBLICATIONS

Korean Intellectual Property Office Application No. 10-2019-0083590, Office Action dated Feb. 2, 2021, 7 pages.

*Primary Examiner* — Carl H Layno
*Assistant Examiner* — Anh-Khoa N Dinh
(74) *Attorney, Agent, or Firm* — Lee Hong Degerman Kang & Waimey

(57) ABSTRACT

A light output device for caring for a skin of a user using artificial intelligence includes a plurality of light sources configured to irradiate light, a memory configured to store a skin care model learned using a deep learning algorithm to infer a facial skin state of the user, a camera configured to capture an image of a face of the user, and a processor configured to acquire a skin state of each part of the face based on a first-type face image captured through the camera and the skin care model, and control light output of the plurality of light sources based on the acquired skin state.

17 Claims, 12 Drawing Sheets

(51) Int. Cl.
  *G06T 7/00* (2017.01)
  *A61B 5/00* (2006.01)
(52) U.S. Cl.
  CPC .... *G06T 7/0012* (2013.01); *A61N 2005/0659* (2013.01); *A61N 2005/0661* (2013.01); *A61N 2005/0663* (2013.01); *G06T 2207/20081* (2013.01); *G06T 2207/20084* (2013.01); *G06T 2207/30088* (2013.01); *G06T 2207/30201* (2013.01)
(58) Field of Classification Search
  CPC .......... A61N 5/0616; A61N 2005/0647; A61N 2005/0659; A61N 2005/0661; A61N 2005/0663; G06K 9/00248; G06T 7/0012; G06T 2207/20081; G06T 2207/20084; G06T 2207/30088; G06T 2207/30201
  See application file for complete search history.

(56) References Cited

U.S. PATENT DOCUMENTS

| | | | | |
|---|---|---|---|---|
| 2012/0209151 | A1* | 8/2012 | Zhou | A61H 23/0245 601/2 |
| 2014/0288351 | A1* | 9/2014 | Jones | A61N 5/0624 600/9 |
| 2019/0030359 | A1* | 1/2019 | Dijkstra | A61B 5/0075 |

FOREIGN PATENT DOCUMENTS

| | | |
|---|---|---|
| KR | 10-1492793 | 2/2015 |
| KR | 10-1522730 | 5/2015 |
| KR | 10-2019-0014728 | 2/2019 |

\* cited by examiner

|  | FRECKLES | PORES | WRINKLES | OIL | PIGMENTATIN | MOISTURE | DAMAGE VULNERABILITY |
|---|---|---|---|---|---|---|---|
| FOREHEAD | 1 | 2 | 3 | 1 | 2 | 1 | 1 |
| LEFT CHEEK | 3 | 3 | 2 | 3 | 3 | 3 | 0 |
| RIGHT CHEEK | 4 | 3 | 3 | 3 | 4 | 3 | 0 |
| NOSE | 2 | 5 | 1 | 4 | 5 | 4 | 1 |
| JAW | 0 | 0 | 1 | 0 | 1 | 2 | 0 |

LIGHT OUTPUT DEVICE FOR CARING FOR USER USING ARTIFICIAL INTELLIGENCE AND METHOD OF OPERATING THE SAME

CROSS-REFERENCE TO RELATED APPLICATIONS

Pursuant to 35 U.S.C. § 119(a), this application claims the benefit of earlier filing date and right of priority to Korean Patent Application No. 10-2019-0083590, filed on Jul. 11, 2019, the contents of which are hereby incorporated by reference herein in its entirety.

BACKGROUND

The present invention relates to a light output device for caring for the skin of a user using artificial intelligence and a method of operating the same.

Skin may be damaged due to aging of cells, repetition of specific facial expressions, continuous exposure to external environments (ultraviolet rays, fine dust, etc.), stress, etc. For example, aging of cells or repetition of specific facial expressions may cause wrinkles of skin and continuous exposure to external environments or stress may cause various troubles such as acne or freckles.

Skin care for preventing or minimizing skin damage aims at removing blemish and keeping clean and soft skin. In particular, the most attention has been paid to skin care of a face among body parts. Accordingly, people have a massage, apply functional cosmetics or keeping their skins clean using various cleaning products, for skin care of their faces.

In particular, in recent years, devices (e.g., mask type skin care devices, etc.) attached to or worn on a user's faces to output light have appeared. Such a light output device may be provided with a plurality of light sources (e.g., LEDs) to output light toward the facial skin of the user.

However, conventionally, since light is uniformly output without considering the skin condition of each part of the user's face, proper skin care cannot be performed.

In addition, outputting light without considering a wound such as scratch may provide a stimulus to the wound.

SUMMARY

An object of the present invention is to provide a light output device capable of performing skin care suitable for each part in consideration of the skin condition of each part of a user's face through artificial intelligence.

Another object of the present invention is to provide a light output device capable of performing efficient skin care, by changing a light irradiation time and a light irradiation intensity according to the skin state of each part.

A light output device for caring for the skin of a user using artificial intelligence according to an embodiment of the present invention can acquire the skin state of each part of the face of the user based on a first-type face image captured through a camera and a skin care model and control light output of a plurality of light sources based on the acquired skin state.

A light output device according to an embodiment of the present invention can determine the skin type of each part and perform control to change a light irradiation time and intensity of a plurality of light sources according to the determined skin type.

DETAILED DESCRIPTION OF THE EMBODIMENTS

<Artificial Intelligence (AI)>

Figure 1:
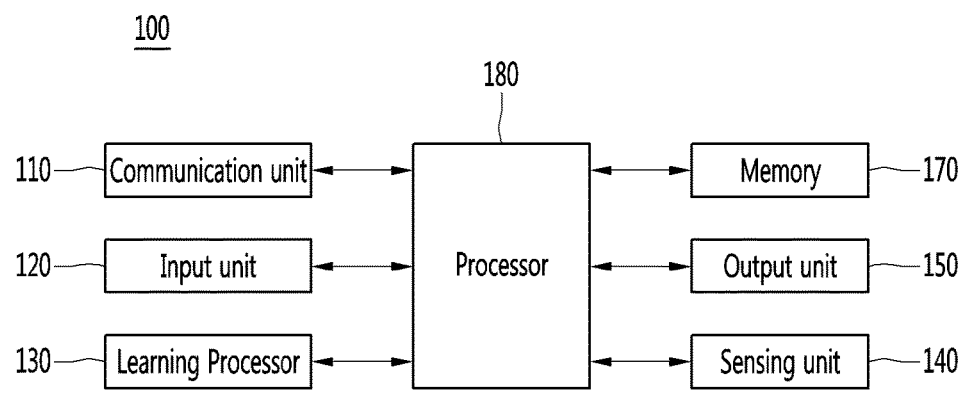
FIG. 1 is a view showing an artificial intelligence (AI) device according to an embodiment of the present invention.

Artificial intelligence refers to the field of studying artificial intelligence or methodology for making artificial intelligence, and machine learning refers to the field of defining various issues dealt with in the field of artificial intelligence and studying methodology for solving the various issues. Machine learning is defined as an algorithm that enhances the performance of a certain task through a steady experience with the certain task.

An artificial neural network (ANN) is a model used in machine learning and may mean a whole model of problem-solving ability which is composed of artificial neurons (nodes) that form a network by synaptic connections. The artificial neural network can be defined by a connection pattern between neurons in different layers, a learning process for updating model parameters, and an activation function for generating an output value.

The artificial neural network may include an input layer, an output layer, and optionally one or more hidden layers. Each layer includes one or more neurons, and the artificial neural network may include a synapse that links neurons to neurons. In the artificial neural network, each neuron may output the function value of the activation function for input signals, weights, and deflections input through the synapse.

Model parameters refer to parameters determined through learning and include a weight value of synaptic connection and deflection of neurons. A hyperparameter means a parameter to be set in the machine learning algorithm before learning, and includes a learning rate, a repetition number, a mini batch size, and an initialization function.

The purpose of the learning of the artificial neural network may be to determine the model parameters that minimize a loss function. The loss function may be used as an index to determine optimal model parameters in the learning process of the artificial neural network.

Machine learning may be classified into supervised learning, unsupervised learning, and reinforcement learning according to a learning method.

The supervised learning may refer to a method of learning an artificial neural network in a state in which a label for learning data is given, and the label may mean the correct answer (or result value) that the artificial neural network must infer when the learning data is input to the artificial neural network. The unsupervised learning may refer to a method of learning an artificial neural network in a state in which a label for learning data is not given. The reinforcement learning may refer to a learning method in which an agent defined in a certain environment learns to select a behavior or a behavior sequence that maximizes cumulative compensation in each state.

Machine learning, which is implemented as a deep neural network (DNN) including a plurality of hidden layers among artificial neural networks, is also referred to as deep learning, and the deep running is part of machine running. In the following, machine learning is used to mean deep running.

<Robot>

A robot may refer to a machine that automatically processes or operates a given task by its own ability. In particular, a robot having a function of recognizing an environment and performing a self-determination operation may be referred to as an intelligent robot.

Robots may be classified into industrial robots, medical robots, home robots, military robots, and the like according to the use purpose or field.

The robot includes a driving unit may include an actuator or a motor and may perform various physical operations such as moving a robot joint. In addition, a movable robot may include a wheel, a brake, a propeller, and the like in a driving unit, and may travel on the ground through the driving unit or fly in the air.

<Self-Driving>

Self-driving refers to a technique of driving for oneself, and a self-driving vehicle refers to a vehicle that travels without an operation of a user or with a minimum operation of a user.

For example, the self-driving may include a technology for maintaining a lane while driving, a technology for automatically adjusting a speed, such as adaptive cruise control, a technique for automatically traveling along a predetermined route, and a technology for automatically setting and traveling a route when a destination is set.

The vehicle may include a vehicle having only an internal combustion engine, a hybrid vehicle having an internal combustion engine and an electric motor together, and an electric vehicle having only an electric motor, and may include not only an automobile but also a train, a motorcycle, and the like.

At this time, the self-driving vehicle may be regarded as a robot having a self-driving function.

<eXtended Reality (XR)>

Extended reality is collectively referred to as virtual reality (VR), augmented reality (AR), and mixed reality (MR). The VR technology provides a real-world object and background only as a CG image, the AR technology provides a virtual CG image on a real object image, and the MR technology is a computer graphic technology that mixes and combines virtual objects into the real world.

The MR technology is similar to the AR technology in that the real object and the virtual object are shown together. However, in the AR technology, the virtual object is used in the form that complements the real object, whereas in the MR technology, the virtual object and the real object are used in an equal manner.

The XR technology may be applied to a head-mount display (HMD), a head-up display (HUD), a mobile phone, a tablet PC, a laptop, a desktop, a TV, a digital signage, and the like. A device to which the XR technology is applied may be referred to as an XR device.

FIG. 1 illustrates an AI device 100 according to an embodiment of the present invention.

The AI device 100 may be implemented by a stationary device or a mobile device, such as a TV, a projector, a mobile phone, a smartphone, a desktop computer, a notebook, a digital broadcasting terminal, a personal digital assistant (PDA), a portable multimedia player (PMP), a navigation device, a tablet PC, a wearable device, a set-top box (STB), a DMB receiver, a radio, a washing machine, a refrigerator, a desktop computer, a digital signage, a robot, a vehicle, and the like.

Referring to FIG. 1, the AI device 100 may include a communication unit 110, an input unit 120, a learning processor 130, a sensing unit 140, an output unit 150, a memory 170, and a processor 180.

The communication unit 110 may transmit and receive data to and from external devices such as other AI devices 100a to 100e and the AI server 200 by using wire/wireless communication technology. For example, the communication unit 110 may transmit and receive sensor information, a user input, a learning model, and a control signal to and from external devices.

The communication technology used by the communication unit 110 includes GSM (Global System for Mobile communication), CDMA (Code Division Multi Access), LTE (Long Term Evolution), 5G, WLAN (Wireless LAN), Wi-Fi (Wireless-Fidelity), Bluetooth™, RFID (Radio Frequency Identification), Infrared Data Association (IrDA), ZigBee, NFC (Near Field Communication), and the like.

The input unit 120 may acquire various kinds of data.

At this time, the input unit 120 may include a camera for inputting a video signal, a microphone for receiving an audio signal, and a user input unit for receiving information from a user. The camera or the microphone may be treated as a sensor, and the signal acquired from the camera or the microphone may be referred to as sensing data or sensor information.

The input unit 120 may acquire a learning data for model learning and an input data to be used when an output is acquired by using learning model. The input unit 120 may acquire raw input data. In this case, the processor 180 or the learning processor 130 may extract an input feature by preprocessing the input data.

The learning processor 130 may learn a model composed of an artificial neural network by using learning data. The learned artificial neural network may be referred to as a learning model. The learning model may be used to an infer result value for new input data rather than learning data, and the inferred value may be used as a basis for determination to perform a certain operation.

At this time, the learning processor 130 may perform AI processing together with the learning processor 240 of the AI server 200.

At this time, the learning processor 130 may include a memory integrated or implemented in the AI device 100. Alternatively, the learning processor 130 may be implemented by using the memory 170, an external memory directly connected to the AI device 100, or a memory held in an external device.

The sensing unit 140 may acquire at least one of internal information about the AI device 100, ambient environment information about the AI device 100, and user information by using various sensors.

Examples of the sensors included in the sensing unit 140 may include a proximity sensor, an illuminance sensor, an acceleration sensor, a magnetic sensor, a gyro sensor, an inertial sensor, an RGB sensor, an IR sensor, a fingerprint recognition sensor, an ultrasonic sensor, an optical sensor, a microphone, a lidar, and a radar.

The output unit 150 may generate an output related to a visual sense, an auditory sense, or a haptic sense.

At this time, the output unit 150 may include a display unit for outputting time information, a speaker for outputting auditory information, and a haptic module for outputting haptic information.

The memory 170 may store data that supports various functions of the AI device 100. For example, the memory 170 may store input data acquired by the input unit 120, learning data, a learning model, a learning history, and the like.

The processor 180 may determine at least one executable operation of the AI device 100 based on information determined or generated by using a data analysis algorithm or a machine learning algorithm. The processor 180 may control the components of the AI device 100 to execute the determined operation.

To this end, the processor 180 may request, search, receive, or utilize data of the learning processor 130 or the memory 170. The processor 180 may control the components of the AI device 100 to execute the predicted operation or the operation determined to be desirable among the at least one executable operation.

When the connection of an external device is required to perform the determined operation, the processor 180 may generate a control signal for controlling the external device and may transmit the generated control signal to the external device.

The processor 180 may acquire intention information for the user input and may determine the user's requirements based on the acquired intention information.

The processor 180 may acquire the intention information corresponding to the user input by using at least one of a speech to text (STT) engine for converting speech input into a text string or a natural language processing (NLP) engine for acquiring intention information of a natural language.

At least one of the STT engine or the NLP engine may be configured as an artificial neural network, at least part of which is learned according to the machine learning algorithm. At least one of the STT engine or the NLP engine may be learned by the learning processor 130, may be learned by the learning processor 240 of the AI server 200, or may be learned by their distributed processing.

The processor 180 may collect history information including the operation contents of the AI apparatus 100 or the user's feedback on the operation and may store the collected history information in the memory 170 or the learning processor 130 or transmit the collected history information to the external device such as the AI server 200. The collected history information may be used to update the learning model.

The processor 180 may control at least part of the components of AI device 100 so as to drive an application program stored in memory 170. Furthermore, the processor 180 may operate two or more of the components included in the AI device 100 in combination so as to drive the application program.

Figure 2:
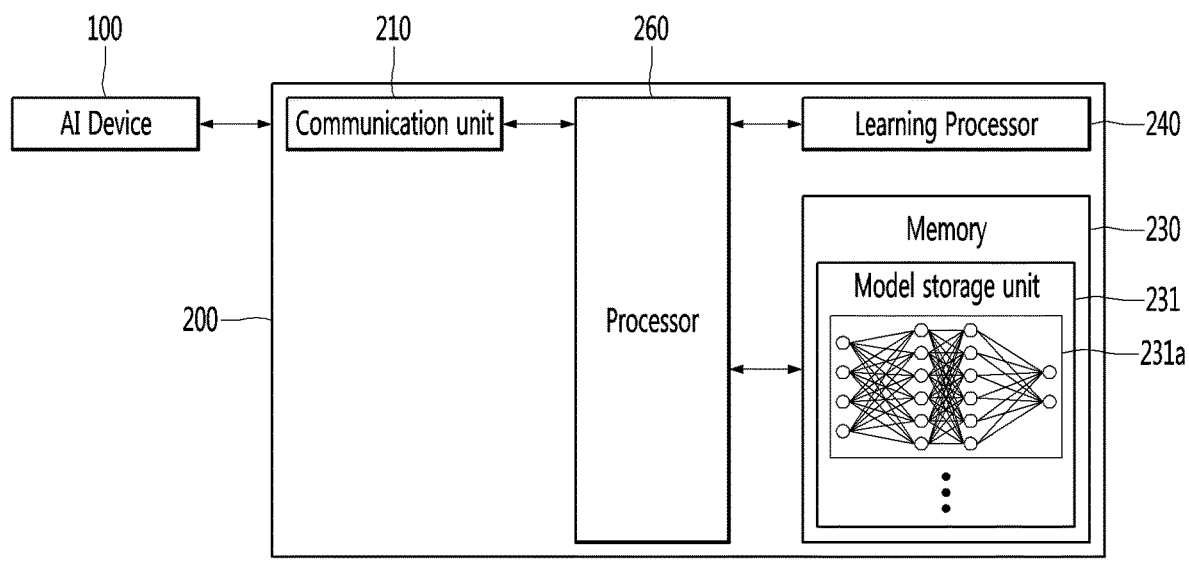
FIG. 2 is a view showing an AI server according to an embodiment of the present invention.

FIG. 2 illustrates an AI server 200 according to an embodiment of the present invention.

Referring to FIG. 2, the AI server 200 may refer to a device that learns an artificial neural network by using a machine learning algorithm or uses a learned artificial neural network. The AI server 200 may include a plurality of servers to perform distributed processing, or may be defined as a 5G network. At this time, the AI server 200 may be included as a partial configuration of the AI device 100, and may perform at least part of the AI processing together.

The AI server 200 may include a communication unit 210, a memory 230, a learning processor 240, a processor 260, and the like.

The communication unit 210 can transmit and receive data to and from an external device such as the AI device 100.

The memory 230 may include a model storage unit 231. The model storage unit 231 may store a learning or learned model (or an artificial neural network 231a) through the learning processor 240.

The learning processor 240 may learn the artificial neural network 231a by using the learning data. The learning model may be used in a state of being mounted on the AI server 200 of the artificial neural network, or may be used in a state of being mounted on an external device such as the AI device 100.

The learning model may be implemented in hardware, software, or a combination of hardware and software. If all or part of the learning models are implemented in software, one or more instructions that constitute the learning model may be stored in memory 230.

The processor 260 may infer the result value for new input data by using the learning model and may generate a response or a control command based on the inferred result value.

Figure 3:
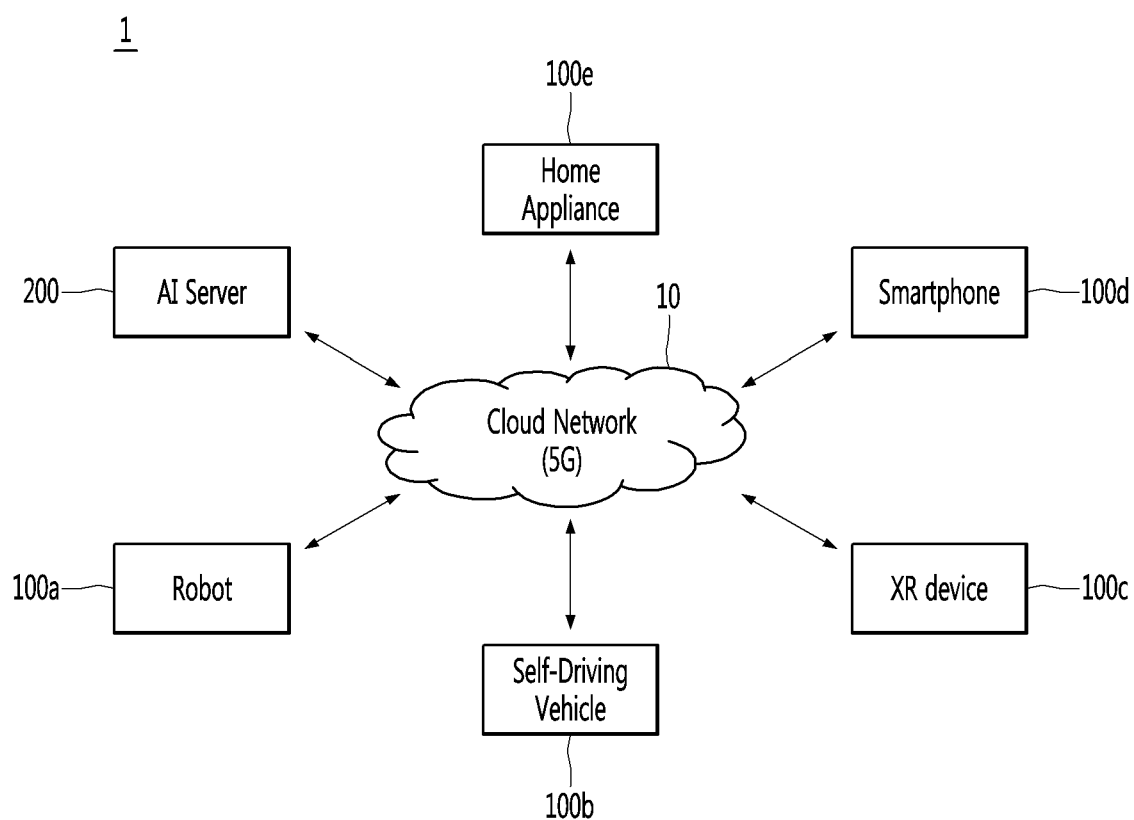
FIG. 3 is a view showing an AI system according to an embodiment of the present invention.

FIG. 3 illustrates an AI system 1 according to an embodiment of the present invention.

Referring to FIG. 3, in the AI system 1, at least one of an AI server 200, a robot 100a, a self-driving vehicle 100b, an XR device 100c, a smartphone 100d, or a home appliance 100e is connected to a cloud network 10. The robot 100a, the self-driving vehicle 100b, the XR device 100c, the smartphone 100d, or the home appliance 100e, to which the AI technology is applied, may be referred to as AI devices 100a to 100e.

The cloud network 10 may refer to a network that forms part of a cloud computing infrastructure or exists in a cloud computing infrastructure. The cloud network 10 may be configured by using a 3G network, a 4G or LTE network, or a 5G network.

That is, the devices 100a to 100e and 200 configuring the AI system 1 may be connected to each other through the cloud network 10. In particular, each of the devices 100a to 100e and 200 may communicate with each other through a base station, but may directly communicate with each other without using a base station.

The AI server 200 may include a server that performs AI processing and a server that performs operations on big data.

The AI server 200 may be connected to at least one of the AI devices constituting the AI system 1, that is, the robot 100a, the self-driving vehicle 100b, the XR device 100c, the smartphone 100d, or the home appliance 100e through the cloud network 10, and may assist at least part of AI processing of the connected AI devices 100a to 100e.

At this time, the AI server 200 may learn the artificial neural network according to the machine learning algorithm instead of the AI devices 100a to 100e, and may directly store the learning model or transmit the learning model to the AI devices 100a to 100e.

At this time, the AI server 200 may receive input data from the AI devices 100a to 100e, may infer the result value for the received input data by using the learning model, may generate a response or a control command based on the inferred result value, and may transmit the response or the control command to the AI devices 100a to 100e.

Alternatively, the AI devices 100a to 100e may infer the result value for the input data by directly using the learning model, and may generate the response or the control command based on the inference result.

Hereinafter, various embodiments of the AI devices 100a to 100e to which the above-described technology is applied will be described. The AI devices 100a to 100e illustrated in FIG. 3 may be regarded as a specific embodiment of the AI device 100 illustrated in FIG. 1.

<AI+Robot>

The robot 100a, to which the AI technology is applied, may be implemented as a guide robot, a carrying robot, a cleaning robot, a wearable robot, an entertainment robot, a pet robot, an unmanned flying robot, or the like.

The robot 100a may include a robot control module for controlling the operation, and the robot control module may refer to a software module or a chip implementing the software module by hardware.

The robot 100a may acquire state information about the robot 100a by using sensor information acquired from various kinds of sensors, may detect (recognize) surrounding environment and objects, may generate map data, may determine the route and the travel plan, may determine the response to user interaction, or may determine the operation.

The robot 100a may use the sensor information acquired from at least one sensor among the lidar, the radar, and the camera so as to determine the travel route and the travel plan.

The robot 100a may perform the above-described operations by using the learning model composed of at least one artificial neural network. For example, the robot 100a may recognize the surrounding environment and the objects by using the learning model, and may determine the operation by using the recognized surrounding information or object information. The learning model may be learned directly from the robot 100a or may be learned from an external device such as the AI server 200.

At this time, the robot 100a may perform the operation by generating the result by directly using the learning model, but the sensor information may be transmitted to the external device such as the AI server 200 and the generated result may be received to perform the operation.

The robot 100a may use at least one of the map data, the object information detected from the sensor information, or the object information acquired from the external apparatus to determine the travel route and the travel plan, and may control the driving unit such that the robot 100a travels along the determined travel route and travel plan.

The map data may include object identification information about various objects arranged in the space in which the robot 100a moves. For example, the map data may include object identification information about fixed objects such as walls and doors and movable objects such as pollen and desks. The object identification information may include a name, a type, a distance, and a position.

In addition, the robot 100a may perform the operation or travel by controlling the driving unit based on the control/interaction of the user. At this time, the robot 100a may acquire the intention information of the interaction due to the user's operation or speech utterance, and may determine the response based on the acquired intention information, and may perform the operation.

<AI+Self-Driving>

The self-driving vehicle 100b, to which the AI technology is applied, may be implemented as a mobile robot, a vehicle, an unmanned flying vehicle, or the like.

The self-driving vehicle 100b may include a self-driving control module for controlling a self-driving function, and the self-driving control module may refer to a software module or a chip implementing the software module by hardware. The self-driving control module may be included in the self-driving vehicle 100b as a component thereof, but may be implemented with separate hardware and connected to the outside of the self-driving vehicle 100b.

The self-driving vehicle 100b may acquire state information about the self-driving vehicle 100b by using sensor information acquired from various kinds of sensors, may detect (recognize) surrounding environment and objects, may generate map data, may determine the route and the travel plan, or may determine the operation.

Like the robot 100a, the self-driving vehicle 100b may use the sensor information acquired from at least one sensor among the lidar, the radar, and the camera so as to determine the travel route and the travel plan.

In particular, the self-driving vehicle 100b may recognize the environment or objects for an area covered by a field of view or an area over a certain distance by receiving the sensor information from external devices, or may receive directly recognized information from the external devices.

The self-driving vehicle 100b may perform the above-described operations by using the learning model composed of at least one artificial neural network. For example, the self-driving vehicle 100b may recognize the surrounding environment and the objects by using the learning model, and may determine the traveling movement line by using the recognized surrounding information or object information. The learning model may be learned directly from the self-driving vehicle 100a or may be learned from an external device such as the AI server 200.

At this time, the self-driving vehicle 100b may perform the operation by generating the result by directly using the learning model, but the sensor information may be transmitted to the external device such as the AI server 200 and the generated result may be received to perform the operation.

The self-driving vehicle 100b may use at least one of the map data, the object information detected from the sensor information, or the object information acquired from the external apparatus to determine the travel route and the travel plan, and may control the driving unit such that the self-driving vehicle 100b travels along the determined travel route and travel plan.

The map data may include object identification information about various objects arranged in the space (for example, road) in which the self-driving vehicle 100b travels. For example, the map data may include object identification information about fixed objects such as street lamps, rocks, and buildings and movable objects such as vehicles and pedestrians. The object identification information may include a name, a type, a distance, and a position.

In addition, the self-driving vehicle 100b may perform the operation or travel by controlling the driving unit based on the control/interaction of the user. At this time, the self-driving vehicle 100b may acquire the intention information of the interaction due to the user's operation or speech utterance, and may determine the response based on the acquired intention information, and may perform the operation.

<AI+XR>

The XR device 100c, to which the AI technology is applied, may be implemented by a head-mount display (HMD), a head-up display (HUD) provided in the vehicle, a television, a mobile phone, a smartphone, a computer, a wearable device, a home appliance, a digital signage, a vehicle, a fixed robot, a mobile robot, or the like.

The XR device 100c may analyzes three-dimensional point cloud data or image data acquired from various sensors or the external devices, generate position data and attribute data for the three-dimensional points, acquire information about the surrounding space or the real object, and render to output the XR object to be output. For example, the XR device 100c may output an XR object including the additional information about the recognized object in correspondence to the recognized object.

The XR device 100c may perform the above-described operations by using the learning model composed of at least one artificial neural network. For example, the XR device 100c may recognize the real object from the three-dimensional point cloud data or the image data by using the learning model, and may provide information corresponding to the recognized real object. The learning model may be directly learned from the XR device 100c, or may be learned from the external device such as the AI server 200.

At this time, the XR device 100c may perform the operation by generating the result by directly using the learning model, but the sensor information may be transmitted to the external device such as the AI server 200 and the generated result may be received to perform the operation.

<AI+Robot+Self-Driving>

The robot 100a, to which the AI technology and the self-driving technology are applied, may be implemented as a guide robot, a carrying robot, a cleaning robot, a wearable robot, an entertainment robot, a pet robot, an unmanned flying robot, or the like.

The robot 100a, to which the AI technology and the self-driving technology are applied, may refer to the robot itself having the self-driving function or the robot 100a interacting with the self-driving vehicle 100b.

The robot 100a having the self-driving function may collectively refer to a device that moves for itself along the given movement line without the user's control or moves for itself by determining the movement line by itself.

The robot 100a and the self-driving vehicle 100b having the self-driving function may use a common sensing method so as to determine at least one of the travel route or the travel plan. For example, the robot 100a and the self-driving vehicle 100b having the self-driving function may determine at least one of the travel route or the travel plan by using the information sensed through the lidar, the radar, and the camera.

The robot 100a that interacts with the self-driving vehicle 100b exists separately from the self-driving vehicle 100b and may perform operations interworking with the self-driving function of the self-driving vehicle 100b or interworking with the user who rides on the self-driving vehicle 100b.

At this time, the robot 100a interacting with the self-driving vehicle 100b may control or assist the self-driving function of the self-driving vehicle 100b by acquiring sensor information on behalf of the self-driving vehicle 100b and providing the sensor information to the self-driving vehicle 100b, or by acquiring sensor information, generating environment information or object information, and providing the information to the self-driving vehicle 100b.

Alternatively, the robot 100a interacting with the self-driving vehicle 100b may monitor the user boarding the self-driving vehicle 100b, or may control the function of the self-driving vehicle 100b through the interaction with the user. For example, when it is determined that the driver is in a drowsy state, the robot 100a may activate the self-driving function of the self-driving vehicle 100b or assist the control of the driving unit of the self-driving vehicle 100b. The function of the self-driving vehicle 100b controlled by the robot 100a may include not only the self-driving function but also the function provided by the navigation system or the audio system provided in the self-driving vehicle 100b.

Alternatively, the robot 100a that interacts with the self-driving vehicle 100b may provide information or assist the function to the self-driving vehicle 100b outside the self-driving vehicle 100b. For example, the robot 100a may provide traffic information including signal information and the like, such as a smart signal, to the self-driving vehicle 100b, and automatically connect an electric charger to a charging port by interacting with the self-driving vehicle 100b like an automatic electric charger of an electric vehicle.

<AI+Robot+XR>

The robot 100a, to which the AI technology and the XR technology are applied, may be implemented as a guide robot, a carrying robot, a cleaning robot, a wearable robot, an entertainment robot, a pet robot, an unmanned flying robot, a drone, or the like.

The robot 100a, to which the XR technology is applied, may refer to a robot that is subjected to control/interaction in an XR image. In this case, the robot 100a may be separated from the XR device 100c and interwork with each other.

When the robot 100a, which is subjected to control/interaction in the XR image, may acquire the sensor information from the sensors including the camera, the robot 100a or the XR device 100c may generate the XR image based on the sensor information, and the XR device 100c may output the generated XR image. The robot 100a may operate based on the control signal input through the XR device 100c or the user's interaction.

For example, the user can confirm the XR image corresponding to the time point of the robot 100a interworking remotely through the external device such as the XR device 100c, adjust the self-driving travel path of the robot 100a through interaction, control the operation or driving, or confirm the information about the surrounding object.

<AI+Self-Driving+XR>

The self-driving vehicle 100b, to which the AI technology and the XR technology are applied, may be implemented as a mobile robot, a vehicle, an unmanned flying vehicle, or the like.

The self-driving driving vehicle 100b, to which the XR technology is applied, may refer to a self-driving vehicle having a means for providing an XR image or a self-driving vehicle that is subjected to control/interaction in an XR image. Particularly, the self-driving vehicle 100b that is subjected to control/interaction in the XR image may be distinguished from the XR device 100c and interwork with each other.

The self-driving vehicle 100b having the means for providing the XR image may acquire the sensor information from the sensors including the camera and output the generated XR image based on the acquired sensor information. For example, the self-driving vehicle 100b may include an HUD to output an XR image, thereby providing a passenger with a real object or an XR object corresponding to an object in the screen.

At this time, when the XR object is output to the HUD, at least part of the XR object may be outputted so as to overlap the actual object to which the passenger's gaze is directed. Meanwhile, when the XR object is output to the display provided in the self-driving vehicle 100b, at least part of the XR object may be output so as to overlap the object in the screen. For example, the self-driving vehicle 100b may output XR objects corresponding to objects such as a lane, another vehicle, a traffic light, a traffic sign, a two-wheeled vehicle, a pedestrian, a building, and the like.

When the self-driving vehicle 100b, which is subjected to control/interaction in the XR image, may acquire the sensor information from the sensors including the camera, the self-driving vehicle 100b or the XR device 100c may generate the XR image based on the sensor information, and the XR device 100c may output the generated XR image. The self-driving vehicle 100b may operate based on the control signal input through the external device such as the XR device 100c or the user's interaction.

Figure 4:
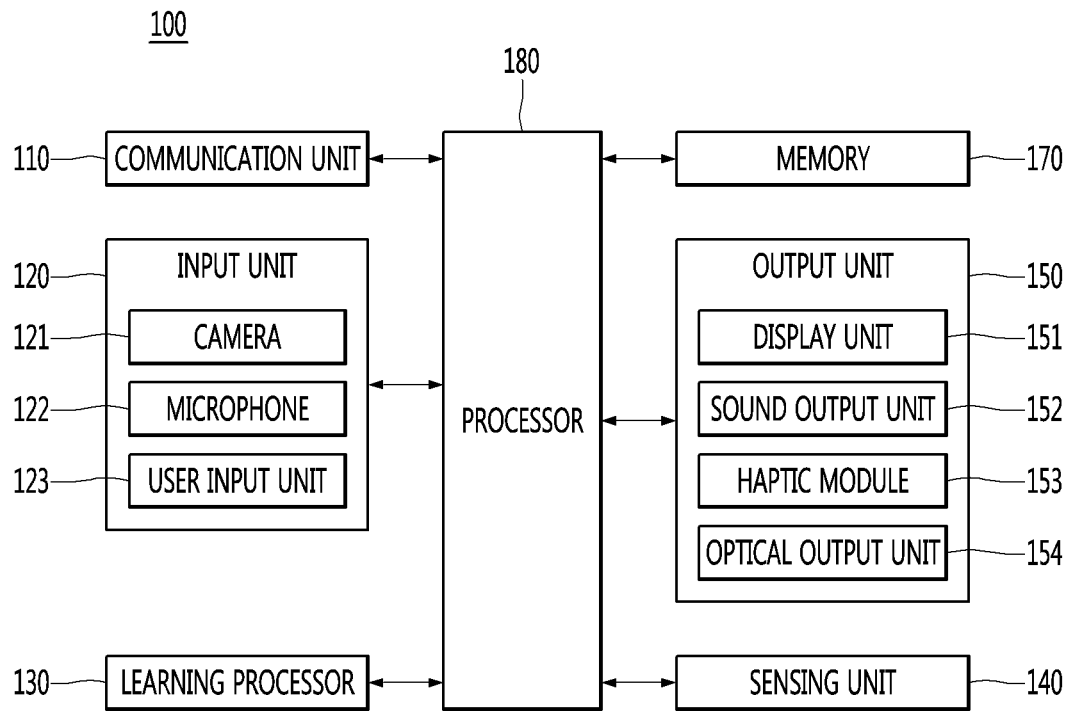
FIG. 4 is a view showing an artificial intelligence (AI) device according to another embodiment of the present invention.

FIG. 4 shows an AI device 100 according to an embodiment of the present invention.

A repeated description of FIG. 1 will be omitted.

Referring to FIG. 4, an input unit 120 may include a camera 121 for receiving a video signal, a microphone 122 for receiving an audio signal and a user input unit 123 for receiving information from a user.

Audio data or image data collected by the input unit 120 may be analyzed and processed as a control command of the user.

The input unit 120 receives video information (or signal), audio information (or signal), data or information received from the user, and the AI device 100 may include one or a plurality of cameras 121 for input of the video information.

The camera 121 processes an image frame such as a still image or a moving image obtained by an image sensor in a video call mode or a shooting mode. The processed image frame may be displayed on a display unit 151 or stored in a memory 170.

The microphone 122 processes external acoustic signals into electrical sound data. The processed sound data may be variously utilized according to the function (or the application program) performed in the AI device 100. Meanwhile, various noise removal algorithms for removing noise generated in a process of receiving the external acoustic signal is applicable to the microphone 122.

The user input unit 123 receives information from the user. When information is received through the user input unit 123, a processor 180 may control operation of the AI device 100 in correspondence with the input information.

The user input unit 123 may include a mechanical input element (or a mechanical key, for example, a button located on a front/rear surface or a side surface of the terminal 100, a dome switch, a jog wheel, a jog switch, and the like) and a touch input element. As one example, the touch input element may be a virtual key, a soft key or a visual key, which is displayed on a touchscreen through software processing, or a touch key located at a portion other than the touchscreen.

An output unit 150 may include at least one of a display unit 151, a sound output unit 152, a haptic module 153, and an optical output unit 154.

The display unit 151 displays (outputs) information processed in the AI device 100. For example, the display unit 151 may display execution screen information of an application program executing at the AI device 100 or user interface (UI) and graphical user interface (GUI) information according to the execution screen information.

The display unit 151 may have an inter-layered structure or an integrated structure with a touch sensor so as to implement a touchscreen. The touchscreen may provide an output interface between the terminal 100 and a user, as well as functioning as the user input unit 123 which provides an input interface between the AI device 100 and the user.

The sound output unit 152 may output audio data received from a communication unit 110 or stored in the memory 170 in a call signal reception mode, a call mode, a record mode, a voice recognition mode, a broadcast reception mode, and the like.

The sound output unit 152 may include at least one of a receiver, a speaker, a buzzer or the like.

The haptic module 153 may generate various tactile effects that can be felt by a user. A representative example of tactile effect generated by the haptic module 153 may be vibration.

The optical output unit 154 may output a signal indicating event generation using light of a light source of the AI device 100. Examples of events generated in the AI device 100 may include a message reception, a call signal reception, a missed call, an alarm, a schedule notice, an email reception, an information reception through an application, and the like.

Figure 5:
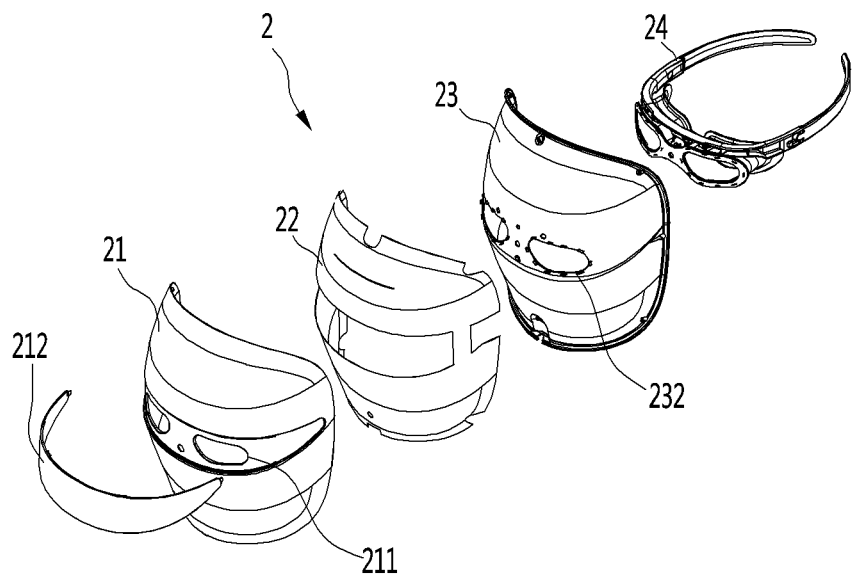
FIG. 5 is an exploded perspective view of a light output device for performing skin care using artificial intelligence according to an embodiment of the present invention.

FIG. 5 is an exploded perspective view of a light output device for performing skin care using artificial intelligence according to an embodiment of the present invention.

Referring to FIG. 5, the light output device 2 for outputting light using artificial intelligence may include a front cover 21, a substrate 22, a rear cover 23 and a wearable device 24.

The substrate 22 may include all the components of the AI device 100 described with reference to FIG. 4. That is, the substrate 22 may include the AI device 100.

The front cover 21 may form the front surface of the light output device 2 and protect the substrate 22 provided between the front cover and the rear cover 23 from external impact or contact. To this end, the front cover 21 may be formed of various types of plastic or ceramics.

Openings 211 for securing a user's view when the user wears the light output device may be formed in the front cover 21. When the user wears the light output device 2, the eyes of the user are located at the openings 211 to secure the view of the user through the openings 211. In some embodiments, an opening protection cover 212 covering the openings 211 may be provided in order to prevent foreign materials from being brought into contact with or colliding with the eyes of the user through the openings 211. The opening protection cover 212 may be formed of a transparent material such as acrylic or plastic.

The substrate 22 may include at least one light source for emitting light for skin care of the user. In some embodiments, the at least one light source may include a plurality of light emitting diodes (LEDs) for outputting light having different colors, in order to output light having different colors according to the operation mode of the light output device 2.

For example, the plurality of LEDs may include at least one red LED and at least one blue LED. The red LED may emit red light having a wavelength of about 645 nm to 670 nm. Red light may facilitate activation of skin cells to effectively improve wrinkles, elasticity and skin tone. Blue LED may emit blue light having a wavelength of about 400 nm to 430 nm. Blue light may effectively remove various types of skin troubles.

Assume that the operation mode of the light output device 2 is divided into an activation mode and a trouble removal mode. When the operation mode is set to the activation mode, the red LED may be activated to emit red light to the skin. In contrast, when the operation mode is set to the trouble removal mode, the blue LED may be activated to emit blue light to the skin. Control of the light source according to the operation mode may be performed by the controller of the light output device 2. In some embodiments, the plurality of LEDs may further include at least one yellow LED. The yellow LED may emit yellow light having a wavelength of about 580 nm to 600 nm and yellow light may more effectively brighten the skin tone.

Similarly to the front cover 21, an opening 221 for securing the user's view when the user wears the light output device may be formed in the substrate 22. As described above, when the user wears the light output device 2, the eyes of the user may be located at the opening 221 to secure the user's view through the opening 221.

Meanwhile, the substrate 22 provided in the light output device 2 having a mask shape may be formed such that at least a portion thereof is curved. To this end, the substrate 22 may be formed of plastic.

The rear cover 23 may be fastened to the front cover 21 and the substrate 22 to cover one surface of the substrate 22. The front cover 21 and the rear cover 23 may prevent water or other foreign materials from permeating into the substrate 22 provided therein, thereby preventing the light source or the other components disposed on the substrate 22 from being damaged or broken.

In addition, when the user wears the light output device 2, the rear cover 23 may be located between the substrate 22 and the user's skin, thereby preventing the user's skin from being brought into contact with the substrate 22.

The rear cover 23 may be formed of a transparent material such as plastic or acrylic, in order to irradiate light emitted from the light source provided in the substrate 22 onto the user's facial skin. In particular, the rear cover 23 may have a structure for uniformly irradiate light emitted from the light source onto the skin or concentrating light to a particular part.

The rear cover 23 may also include openings 232 for securing the user's view similar to the front cover 21 and the substrate 22.

The wearable device 24 may fix the light output device 2 to the user when the user wears the light output device 2. The wearable device 24 may be fastened to the rear cover 23. For example, the wearable device 24 may have an eyeglass shape and may be seated on the user's nose and ears.

In particular, the wearable device 24 according to the embodiment of the present invention may include a wearing detection sensor for effectively detecting whether the user wears the light output device.

Figure 6:
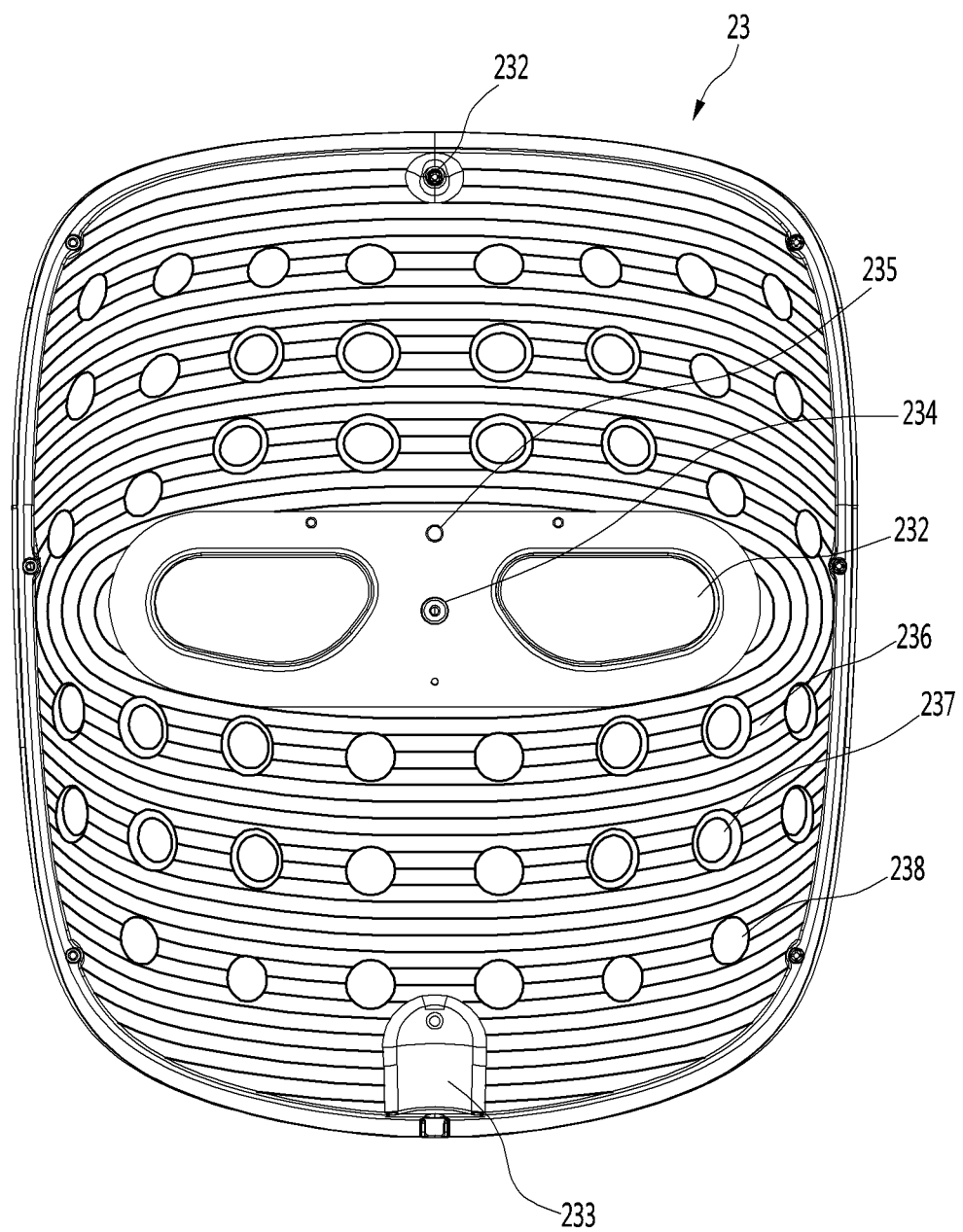
FIG. 6 is a view showing a configuration of rear cover according to an embodiment of the present invention.

Referring to FIG. 6, the rear cover 23 may include the opening 231, a fastener 232, a connector 233 for connecting a user operation device 4 with the substrate 22, a wearable device fastener 234 and a wearing detection sensor connector 235.

As described above with reference to FIG. 2, the opening 231 may be formed to secure the user's view when the user wears the light output device 2.

The rear cover 23 may be fastened with the front cover 21 and the substrate 22 through the fastener 232. For example, the fastener 232 may include a fastening hole and a screw penetrating through the fastening hole, without being limited thereto. As the rear cover 23 is fastened with the front cover 21 and the substrate 22 through the fastener 232, the substrate 22 may be surrounded by the front cover 21 and the rear cover 23, thereby being protected.

The wearable device 24 may be fastened with the rear cover 23 through the wearable device fastener 234 of the rear cover 23. For example, as shown in FIG. 5, the wearable device fastener 234 may be implemented as a fastening groove having a specific shape, and a fastener having a shape corresponding to the fastening groove may be provided in the wearable device 24, such that the wearable device 24 and the rear cover 23 may be fastened. Although one wearable device fastener 234 is shown as being formed at the rear cover 23 in FIG. 5, a plurality of wearable device fasteners may be formed in some embodiments.

The wearing detection sensor connector 235 may be formed to electrically connect the substrate 22 with the wearing detection sensor 245 or the user operation device 4 with the wearing detection sensor 245. The wearing detection sensor connector 235 may be formed at a position corresponding to the position of the wearing detection sensor 245. For example, the wearing detection sensor connector 235 may be implemented as a contact pad having conductivity or a connection hole, through which a cable for connecting the wearing detection sensor 245 with the substrate 22 passes.

In the rear cover 23 according to the embodiment of the present invention, a groove 236, a first lens 237 and a second lens 238 may be formed.

A plurality of light sources may be disposed on the substrate 22 to be spaced apart from each other. For example, a distance between the light sources disposed on the substrate 22 may be determined based on the light irradiation angle of the light source. For example, when the light sources are arbitrarily disposed without considering the light irradiation angle, light emitted from the light sources may not be uniformly irradiated onto the user's skin or many light sources may be unnecessarily provided to reduce power efficiency. According to the embodiment of the present invention, the light sources are disposed on the substrate 22 based on the light irradiation angle of the light source, such that the number of light sources disposed on the light output device 2 is optimized, thereby reducing unnecessary power consumption and increasing skin care efficiency.

When the plurality of light sources spaced apart from each other emits light, the intensity of light irradiated onto the skin at the position corresponding to the position of the light source may be greater than that of light irradiated onto the skin at the position corresponding to a position where the light source is not disposed. That is, as light is ununiformly irradiated onto the user's skin, the skin care effect of the light output device 2 may deteriorate.

Meanwhile, a lot of wrinkles or troubles may be formed in a specific skin part as compared to the other skin parts. For example, a lot of wrinkles may be formed in the forehead of the user as compared to the other parts and a lot of freckles or sun spots may be formed in the cheek of the user as compared to the other parts. In this case, the light output device 2 needs to irradiate relatively more light to a particular part such as the user's forehead or cheek, thereby maximizing the skin care effect.

The groove 236 may be entirely formed in the remaining part except for parts in which the lenses 237 and 238 of the rear cover 23 and the wearable device 24 are installed. For example, the groove 236 may be formed by curving or irregularly forming the surface of the rear cover 23, thereby dispersing light emitted from the light sources when the light passes through the groove 236. As a result, light is uniformly irradiated onto the user's skin, thereby improving the skin care effect on various parts of the face of the user.

Meanwhile, the first lens 237 and the second lens 238 may be disposed on the rear cover 23 to correspond to the positions of the plurality of light sources disposed on the substrate 22. For example, the first lens 237 may be a convex lens and the second lens 238 may be a planar lens.

In particular, the first lens 237 may be disposed to correspond to a part having a relatively high probability of occurrence of wrinkles or troubles, such as forehead or cheek.

Figure 7:
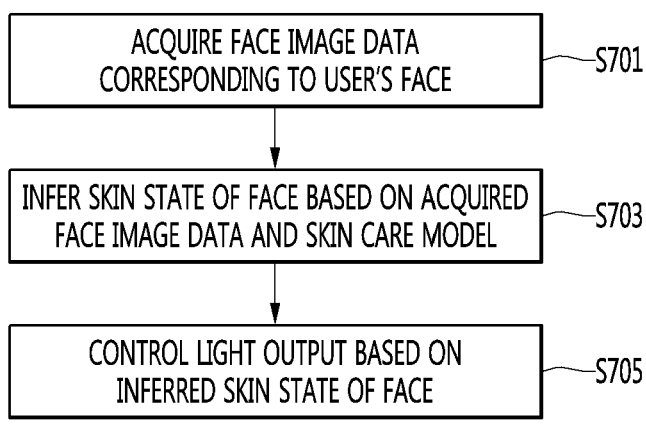
FIG. 7 is a view illustrating a method of operating a light output device for performing skin diagnosis and skin care using artificial intelligence according to an embodiment of the present invention.

FIG. 7 is a view illustrating a method of operating a light output device for performing skin diagnosis and skin care using artificial intelligence according to an embodiment of the present invention.

The light output device 2 may include the components of the AI device 100 of FIG. 4.

The processor 180 of the light output device 2 acquires face image data corresponding to the user's face (S701).

The camera 121 provided in the light output device 2 may capture the image of the user's face. The camera 121 may be disposed adjacent to the wearing detection sensor connector 235 shown in FIG. 6.

When detecting that the light output device 2 is seated on the user's face, the processor 180 may operate the camera 121 to capture the image of the user's face.

The processor 180 may convert the captured image of the user's face into an electrical signal to acquire the face image data.

The processor 180 of the light output device 2 infers the face state of the user based on the acquired face image data and a skin care model (S703).

The processor 180 may output the facial skin state of the user using the face image data as input data and the skin care model.

The facial skin state of the user may include skin states respectively corresponding to a plurality of main parts configuring the face.

The skin care model may be an artificial neural network based model learned by a deep learning algorithm or a machine learning algorithm.

The skin care model may be learned by the learning processor 240 of the AI server 200. In this case, the communication unit 110 of the light output device 2 may receive the skin care model from the AI server 200 and store the received skin care model in the memory 170.

The skin care model will be described below in detail.

The processor 180 of the light output device 2 controls light output of the plurality of light sources disposed on the substrate 22 based on the inferred face state (S705).

The processor 180 may control operation of the plurality of light sources according to the skin states of the plurality of main parts.

The processor 180 may change the intensities of the light sources or the irradiation times of the light sources to perform skin care corresponding to the skin states of the main parts.

This will be described below in detail.

Figure 8:
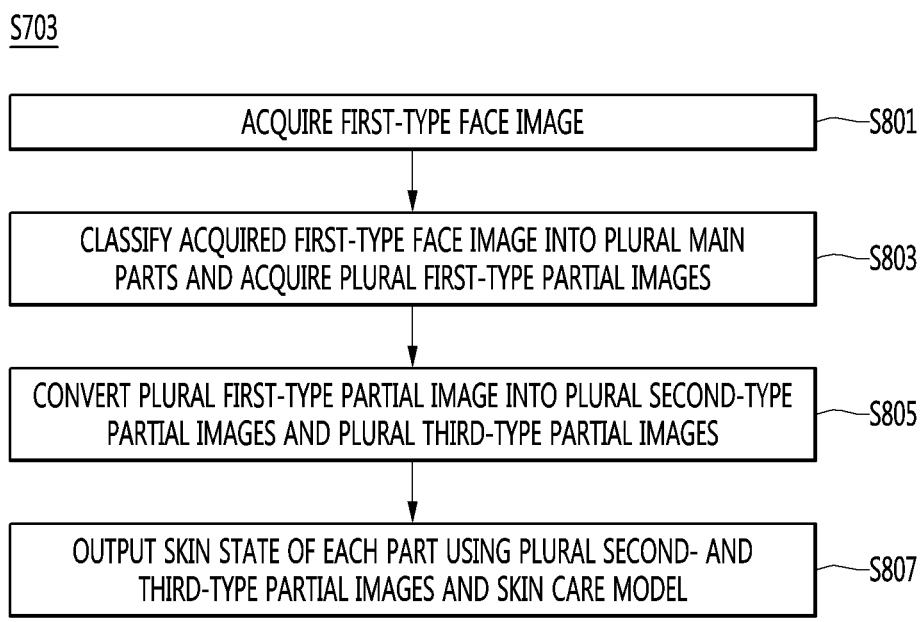
FIG. 8 is a view illustrating a process of outputting the facial skin state of the user through a skin care model according to an embodiment of the present invention in greater detail.

FIG. 8 is a view illustrating a process of outputting the facial skin state of the user through a skin care model according to an embodiment of the present invention in greater detail.

In particular, FIG. 8 is a view illustrating step S703 of FIG. 7 in detail.

The processor 180 acquires a first-type face image (S801).

In one embodiment, the first-type face image may be an RGB-type image captured through the camera 121.

In another example, the first-type face image may be an RGB-type image captured through the smartphone of the user.

Step S801 may correspond to step S701.

The processor 180 classifies the acquired first-type face image into a plurality of main parts to acquire a plurality of first-type partial images (S803).

The plurality of main parts may include a forehead, a nose, a jaw, and a left cheek.

The processor 180 may extract a forehead image, a nose image, a jaw image, a right cheek and a left cheek image from the first-type face image.

This will be described with reference to FIG. 9.

Figure 9:
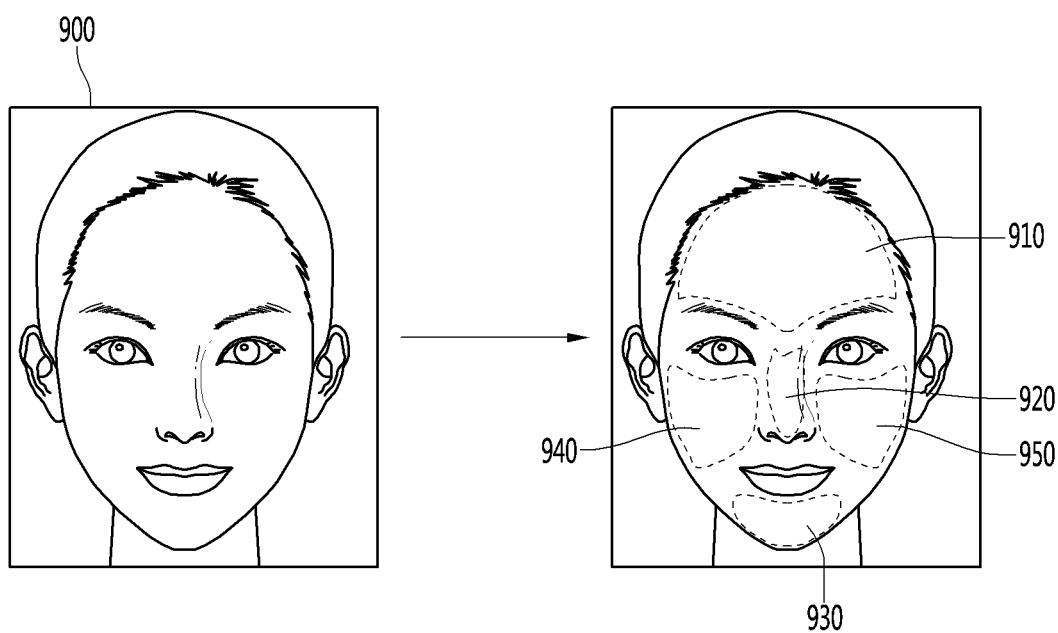
FIG. 9 is a view illustrating a process of extracting a plurality of partial images from the first-type face image according to an embodiment of the present invention.

FIG. 9 is a view illustrating a process of extracting a plurality of partial images from the first-type face image according to an embodiment of the present invention.

Referring to FIG. 9, the first-type face image 900 is shown.

The first-type face image 900 may be an RGB-type image.

The processor 180 may classify the first-type face image 900 into a plurality of first-type partial images 910 to 950 using a block extraction scheme.

The block extraction scheme may refer to a scheme for classifying a face image into a plurality of blocks, extracting feature points from the plurality of classified blocks and extracting main part images from the face image.

The processor 180 may classify the face image into main part areas based on the feature points and extract the main part images through coordinates of the classified main part areas.

In addition, a known scheme for extracting the main parts from the face image 900 may be used.

The plurality of classified first-type partial images may include a forehead image 910, a nose image 920, a jaw image 930, a left cheek image 940 and a right cheek image 950.

FIG. 8 will be described again.

The processor 180 converts the plurality of acquired first-type partial images into a plurality of second-type partial images and a plurality of third-type images (S805).

The second- and third-type images may be used to diagnose the state of the skin.

The second type may be an infrared (IR) image and the third type may be an ultraviolet (UV) image.

The processor 180 may convert the first-type partial image into the second-type partial image and convert the first-type partial image into the third-type partial image, using an image conversion model.

The image conversion model may be an artificial neural network based model learned using a deep learning algorithm or a machine learning algorithm.

The image conversion model may be a model for converting an RGB-type image into an IR-type image or a UV-type image through a mapping function. The mapping function may be used to map the RGB-type image and the IR-type image on a topology basis or to map the RGB-type image and the UV-type image on a topology basis.

The image conversion model may use a known deep learning based generative adversarial network (GAN) algorithm.

The GAN may be an artificial neural network for performing learning through competition between two neural network models and outputting a result. The two neural network models include a generator and a discriminator.

The generator may learn real data and generate false data based on the real data, and the discriminator may perform learning to determine whether the false data of the generator is real or false.

The generator receives and learns data which has failed to deceive the discriminator, and the discriminator receives and learns data which has been deceived by the generator. By repeating this process, false data close to real data may be generated.

The image conversion model may generate an IR-type image or a UV-type image close to reality corresponding to RGB-type image.

This will be described with reference to FIGS. 10 and 11.

Figure 10:
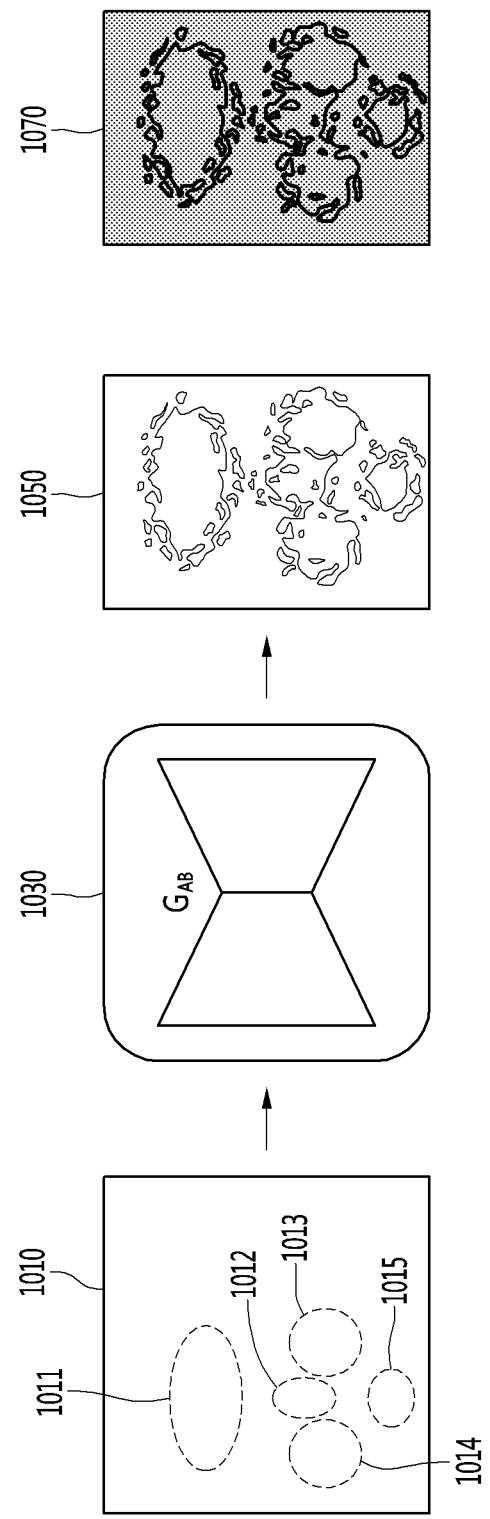
FIG. 10 is a view illustrating an image conversion model for converting first-type partial images into second- and third-type partial images according to an embodiment of the present invention.
Figure 11:
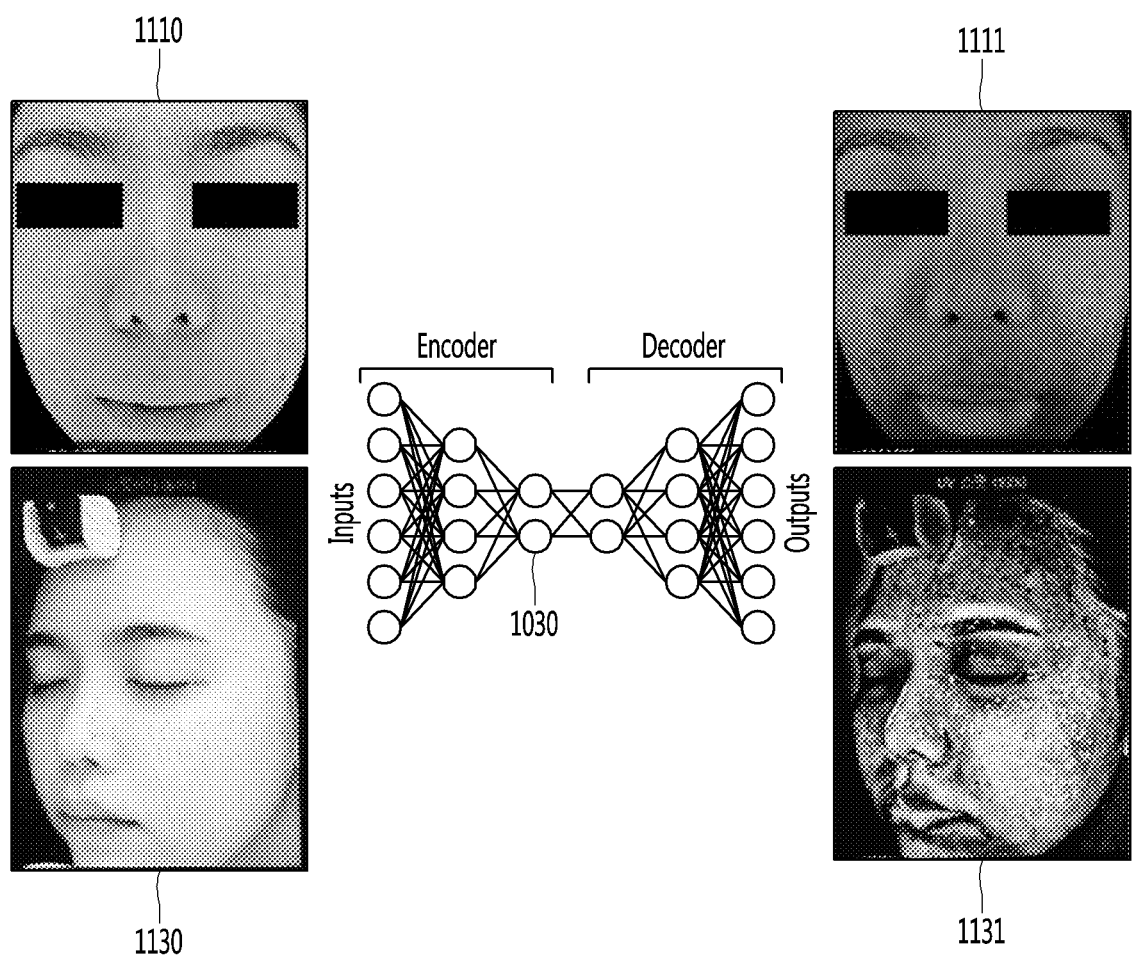
FIG. 11 is a view showing an actual output result of an image conversion model.

FIG. 10 is a view illustrating an image conversion model for converting first-type partial images into second- and third-type partial images according to an embodiment of the present invention and FIG. 11 is a view showing an actual output result of an image conversion model.

Referring to FIG. 10, the first-type partial image 1010 including a plurality of first-type partial images 1011 to 1015 may be input to the image conversion model 1030.

The image conversion model 1030 may convert the first-type partial image set 1010 into a second-type partial image set 1050 and a third-type partial image set 1070 using the GAN.

The image conversion model 1030 may be learned to determine optimal constants of a mapping function used to convert a first-type image into a second-type image.

The image conversion model 1030 may be learned to determine optimal constants of a mapping function used to convert a first-type image into a third-type image.

The second-type partial image set 1050 may include IR-type partial images respectively corresponding to a plurality of first-type partial images 1011 to 1015 and the third-type partial image set 1070 may include UV-type partial images respectively corresponding to the plurality of first-type partial images 1011 to 1015.

The IR-type images and the UV-type images may be used to predict the skin state of each part.

Referring to FIG. 11, an actual example of converting an RGB-type image into an IR-type image or a UV-type image through the image conversion model 1030 is shown.

A first RGB-type image 1110 may be converted into an IR-type image 1111 through the image conversion model 1030.

A second RGB-type image 1130 may be converted into a UV-type image 1131 through the image conversion model 1030.

As the RGB-type image is converted into the IR-type image and the UV-type image, it is possible to easily check the facial skin state of the user.

FIG. 8 will be described again.

The processor 180 outputs the skin state of each part using the plurality of second- and third-type partial images and the skin care model (S807).

The skin care model may refer to a model for determining the values of the skin state variables indicating the states of the skin using the second-type partial image and the third-type partial image as input data.

The variables indicating the states of the skin may include oil, freckles, pores, wrinkles, damage, pigmentation, elasticity and moisture.

The skin care model may be an artificial neural network based on model learned through a deep learning algorithm or a machine learning algorithm.

The processor 180 may acquire the values of the skin state variables as output data using the second-type partial images and the third-type partial images as the input data of the skin care model.

The skin care model may infer the values of optimal skin state variables through supervised learning.

The skin care model may be described with reference to FIG. 12.

Figure 12:
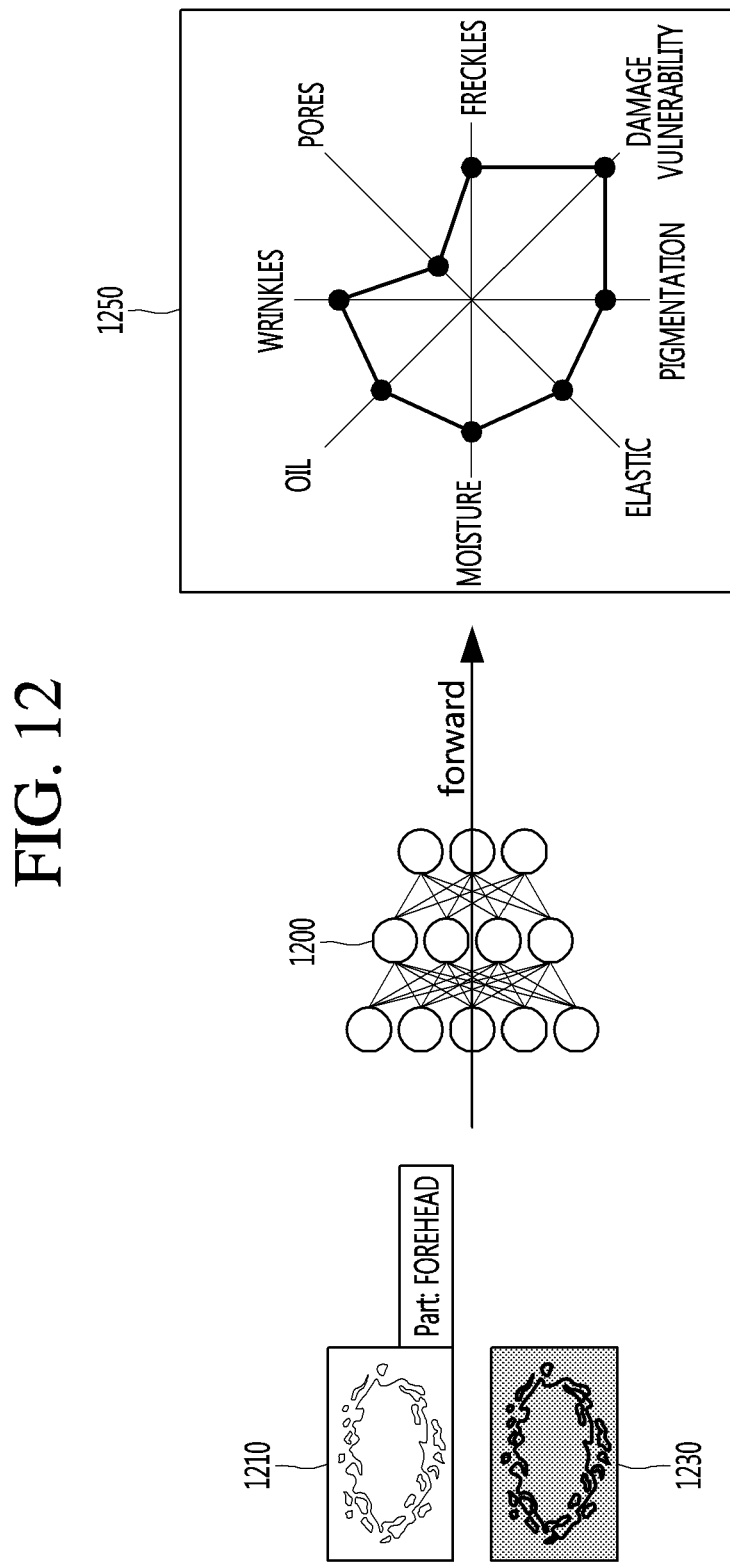
FIG. 12 is a view illustrating a skin care model according to an embodiment of the present invention.

FIG. 12 is a view illustrating a skin care model according to an embodiment of the present invention.

Learning data for learning of the skin care model 1200 may include the second- and third-type partial image data (partial image data set) corresponding to the parts configuring the face and the values of the skin state variables.

Labeling data labeled in the partial image data set may be the values of the skin state variables.

When an input feature vector is extracted from a partial image data set for learning and is input to the skin care model 1200, a skin state result indicating a skin state may be output as a target feature vector.

Meanwhile, the pixel image data of the partial image data set for learning may be input to the skin care model 1200 in pixel units.

The skin care model 1200 may be learned to minimize the value of the cost function corresponding to a difference between the output target feature vector and the labeled skin state.

When the value of the cost function is minimized, the values of the parameters configuring the cost function may be optimized.

For example, the target feature point of the skin care model 1200 may be composed of an output layer including a plurality of nodes indicating the skin state.

The artificial neural network of the skin care model 1200 may be composed of a pixel-wise attribute-aware correction map or a convolution neutral network (CNN).

Referring to FIG. 12, an IR-type partial image 1210 corresponding to a forehead and a UV-type partial image 1230 may be input to a learned skin care model 1200.

As the IR-type partial image 1210 and the UV-type partial image 1230 are input, the skin care model 1200 may output a set 1250 of the values of the skin state variables indicating the skin states.

The set 1250 of the values of the skin state variables include the amount of oil, a degree of wrinkles, the size of pores, a degree of freckles, the number of scarred spots, a degree of pigmentation, a degree of elasticity, and the amount of moisture.

In this manner, the skin states of the forehead, the nose, the jaw, the left cheek and the right cheek may be output.

The values of the skin state variables may be used to determine the irradiation times and intensities of the plurality of light sources when the user wears the light output device 2.

The skin care model 1200 may be learned by the learning processor 240 of the AI server 200.

The light output device 2 may receive the skin care model 1200 from the AI server 200 and store the received skin care model 1200 in the memory 170.

The light output device 2 may output the skin states using the skin care model 1200 stored in the memory 170.

In another embodiment, the light output device 2 may transmit an image captured through the camera 121 to the AI server 200.

The AI server 200 may store the learned image conversion model and the skin care model, analyze the received image using the stored models, and infer the skin states according to the result of analysis.

The processor 180 may control the plurality of light sources to output light suitable for the skin states of the main parts, when the skin states of the main parts of the face are acquired.

This will be described with reference to FIGS. 13 to 15.

Figures 13, 14:
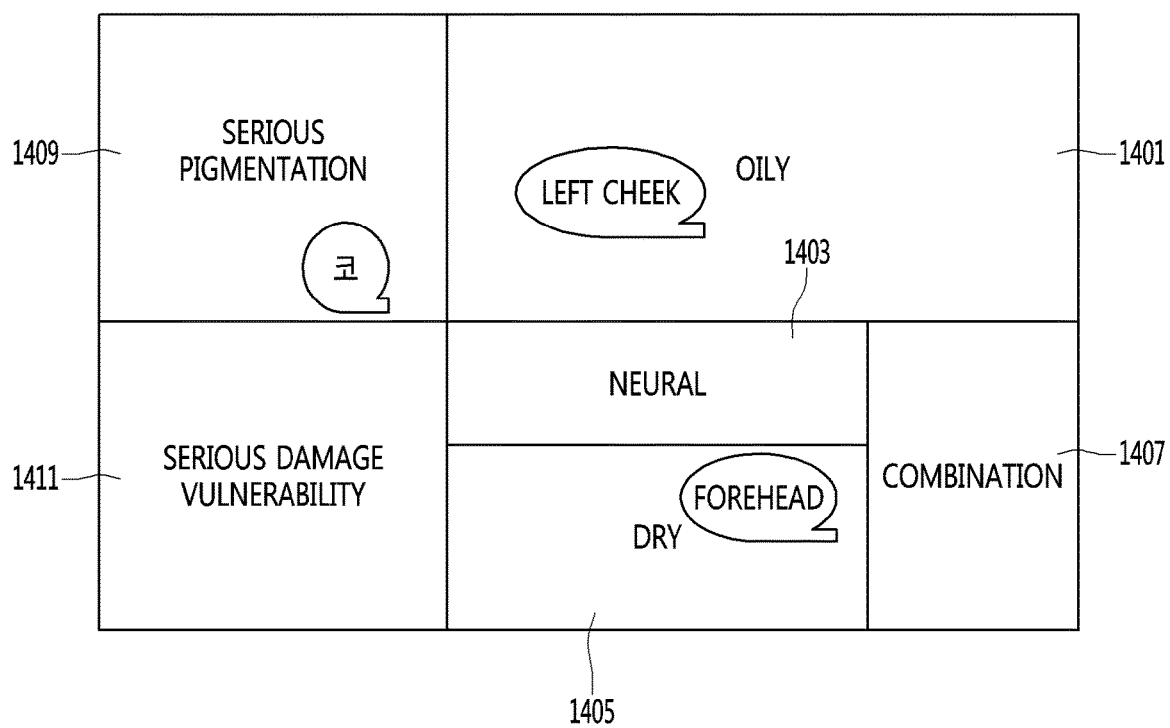
FIG. 13 shows a skin state table indicating the skin states of the parts obtained according to the image data input to the skin care model.
FIG. 14 shows normal types of the skin and the damage types of the skin.
Figure 15:
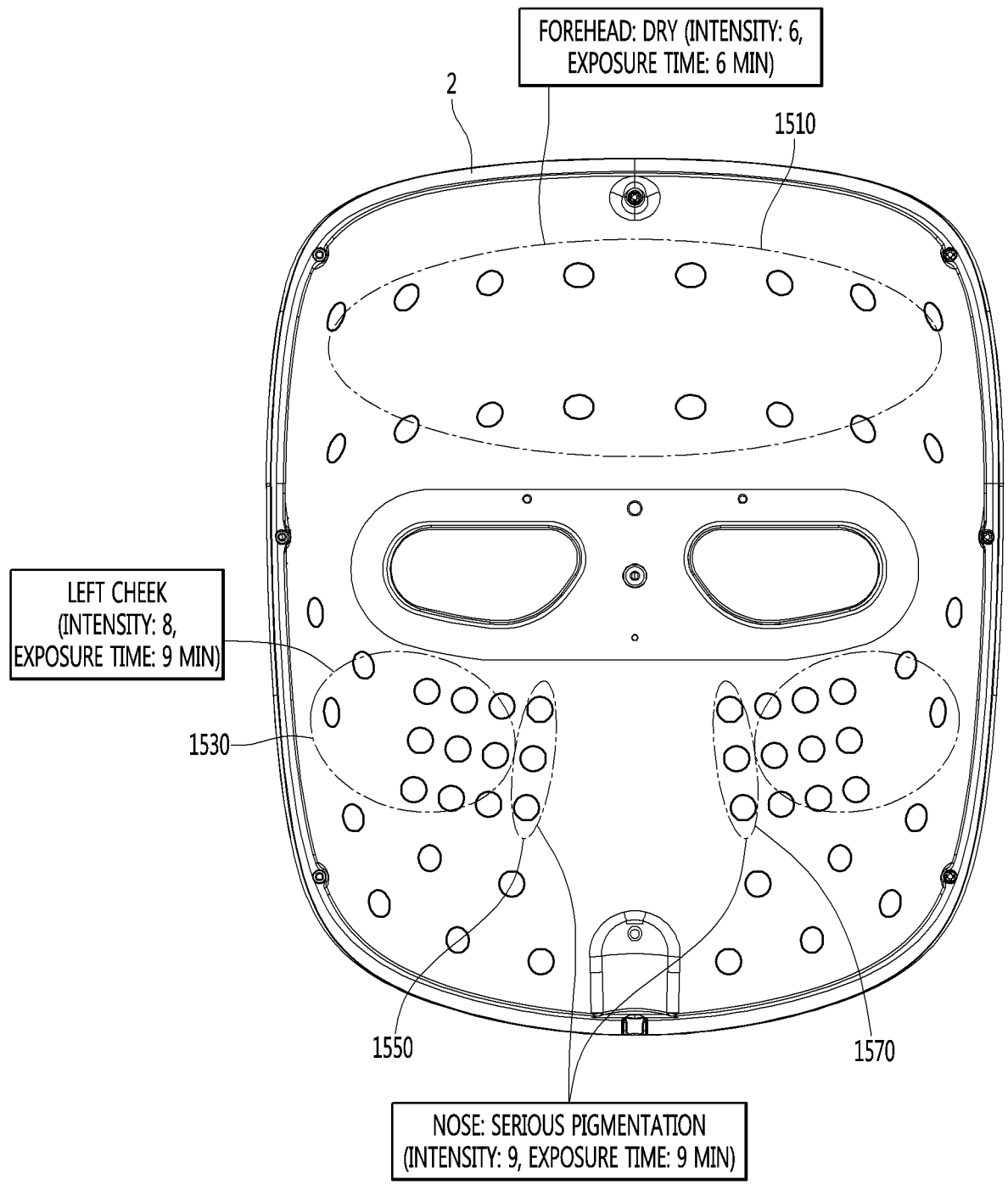
FIG. 15 is a view illustrating an example of changing light output according to the determined skin type of each part according to an embodiment of the present invention.

FIGS. 13 to 15 are views illustrating a care process according to the skin state of each part according to an embodiment of the present invention.

First, FIG. 13 will be described.

FIG. 13 shows a skin state table 1300 indicating the skin states of the parts obtained according to the image data input to the skin care model 1200.

The skin state table 1300 includes the values of the skin state variables indicating the skin states of the forehead, the left cheek, the right cheek, the nose and the jaw.

The skin state variables may include freckles, pores, wrinkles, oil, pigmentation, moisture, and elasticity.

The processor 180 may determine the skin type of each part and the damage type of the skin using the skin state table 1300.

FIG. 14 shows normal types of the skin and the damage types of the skin.

The normal type of the skin may be any one of an oily type 1401, a neural type 403, a dry type 1405 or a combination type 1407.

The normal type of the skin may be determined according to oil or moisture f each part.

For example, when the amount of oil of a particular part is equal to or greater than a certain value and the amount of moisture is less than a certain value, the normal type of the part may be determined as an oily type.

When the amount of oil of a particular part is equal to or greater than a certain value and the amount of moisture is equal to or greater than a certain value, the normal type of the part may be determined as a neural type.

When the amount of oil of a particular part is less than a certain value and the amount of moisture is less than a certain value, the normal type of the part may be determined as a dry type.

When the amount of oil of a particular part is less than a certain value and the amount of moisture is equal to or greater than a certain value, the normal type of the part may be determined as a combination type.

The damage type of the skin may be any one of a serious pigmentation type 1049 or a serious damage vulnerability type 1411.

The particular part may have any one of the normal types or any one of the damage types. Of course, the particular part may have a duplicate type such as one of the normal types and one of the damage types.

In another example, the damage types of the skin have higher priority over the normal types of the skin.

That is, when the particular part is classified as any one of the normal types of the skin and is classified as any one of the damage types of the skin, the particular part may be classified as any one of the damage types of the skin.

For example, when the normal type of the nose is an oily type 1401 and the damage type of the nose is a serious pigmentation type 1409, the processor 180 may determine the nose as the serious pigmentation type 1409.

When the degree of pigmentation is equal to or greater than a certain degree of pigmentation, the processor 180 may determine the damage type of the skin of the part as the serious pigmentation type 1409 regardless of the normal type of the skin.

When the degree of damage vulnerability is equal to or greater than a certain degree of vulnerability, the processor 180 may determine the damage type of the skin of the part as the serious damage vulnerability type 1411 regardless of the normal type of the skin.

When the degree of pigmentation is equal to or greater than the certain degree of pigmentation and the degree of damage vulnerability is equal to or greater than a certain degree of vulnerability, the processor 180 may determine the damage type of the skin as the serious pigmentation type 1409 and the serious damage vulnerability type 1411 regardless of the normal type of the skin.

A process of determining the type of each part will be described with reference to FIGS. 13 and 14.

Although it is assumed that the certain degree of pigmentation used is 5 and the certain degree of vulnerability is 2 as a criterion of the damage type of the skin, this is merely an example.

First, in the case of the nose, when the degree of pigmentation is equal to or greater than the certain degree of pigmentation (5), the processor 180 may determine the damage type of the nose as the serious color pigmentation type 1409.

In the case of the left cheek, since the degree of pigmentation (3) is less than the certain degree of pigmentation (5) and the degree of damage vulnerability (0) is less than the certain degree of vulnerability (2), the processor 180 may not determine the damage type of the left cheek and may determine only the normal type. In this case, the left cheek may be determined as an oily type.

In the case of the forehead, since the degree of pigmentation (2) is less than the certain degree of pigmentation (5) and the degree of damage vulnerability (1) is less than the certain degree of vulnerability (2), the processor 180 may not determine the damage type of the forehead and may determine only the normal type. In this case, the forehead may be determined as a dry type.

When the type of the skin of each part is determined, the processor 180 may determine the light output mode corresponding to the determined type of the skin.

The light output mode may include a normal care mode and a concentrated care mode.

When the skin type of the part belongs to only the normal type, the processor 180 may determine the light output mode as the normal care mode.

When the skin type of the part does not belong to the normal type and belongs to the damage type of the skin, the processor 180 may determine the light output mode as the concentrated care mode.

The normal care mode may refer to a care mode in which the irradiation intensity of the plurality of light sources is in a first intensity range and the irradiation time is in a first time range.

Even in the normal care mode, the irradiation intensity and time may be divided into a plurality of levels according to the form of the normal type.

The concentrated care mode may refer to a care mode in which the irradiation intensity of the plurality of light sources is in a second intensity range and the irradiation time is in a second time range.

Even in the concentrated care mode, the irradiation intensity and time may be divided into a plurality of levels according to the degree of pigmentation and the degree of damage vulnerability of the skin.

The second intensity range may be greater than the first intensity range and the second time range may be greater than the first time range.

FIG. 15 is a view illustrating an example of changing light output according to the determined skin type of each part according to an embodiment of the present invention.

In FIG. 15, assume that the normal care mode is determined with respect to the forehead and the left cheek and the concentrated care mode is determined with respect to the nose.

First, when the skin type of the forehead is determined as the dry type, the processor 180 may set the irradiation intensity of the plurality of light sources disposed in the forehead area 1510 corresponding to the forehead to 6 and set the irradiation time (exposure time) to 6 minutes.

When the skin type of the left cheek is determined as an oily type, the processor 180 may set the irradiation intensity of the plurality of light sources disposed in the left cheek area 1530 corresponding to the left cheek to 8 and set the irradiation time to 9 minutes.

When the skin type of the nose is determined as an serious pigmentation type, the processor 180 may set the irradiation intensity of the plurality of light sources disposed in the nose areas 1550 and 1570 corresponding to the nose to 9 and set the irradiation time to 9 minutes.

When the light output device 2 is seated on the user's face, the processor 180 may control the plurality of light sources to output light to each part with the determined intensity during the determined irradiation time.

According to the embodiment of the present invention, it is possible to output proper light according to the skin state of each part configuring the face and to efficiently care for the skin of the user's face.

Figure 16:
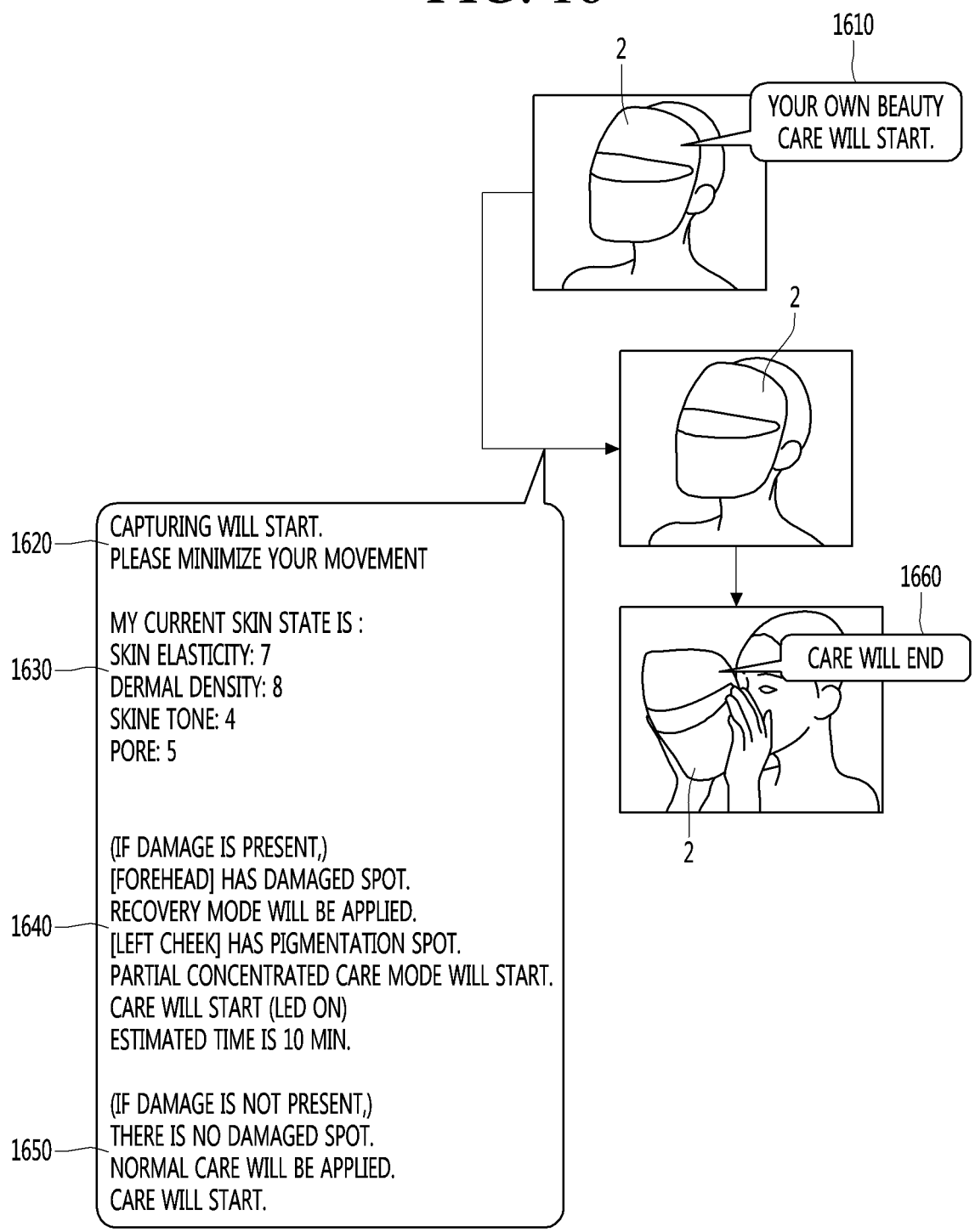
FIG. 16 is a view showing a notification output after a user wears a light output device according to an embodiment of the present invention.

FIG. 16 is a view showing a notification output after a user wears a light output device according to an embodiment of the present invention.

When the light output device 2 is seated on the user's face, the light output device 2 may output a first notification 1610 indicating that personalized beauty care will start through the sound output unit 152.

In addition, after the light output device 2 is seated on the user's face, the light output device 2 may output a second notification 1620 for providing a guide to capturing of the user's face.

The light output device 2 may measure the skin state based on the captured user's face. This was described in step S703 of FIG. 7.

The light output device 2 may output a third notification 1530 indicating the measured skin state. The third notification 1630 may include the values of the skin state variables indicating the skin states.

When a particular part of the face is determined as a serious damage vulnerability type or a serious pigmentation type, the light output device 2 may output a fourth notification 1640 indicating the damage type of the skin and the light output mode. The fourth notification 1640 may further include a light irradiation time and an irradiation intensity.

Meanwhile, when the skin type of each of the plurality of parts of the face is not determined as the damage type, the light output device 2 may output a fifth notification 1650 indicating that the normal care mode is applied.

When skin care is finished, the light output device 2 may output a sixth notification 1660 indicating that skin care is finished.

According to the embodiment of the present invention, the user may receive a feedback on the skin state invisible to the naked eye, by only wearing the light output device 2.

In addition, since care optimized for the personal skin state can be provided through skin diagnosis of the part of the face of an individual, it is possible to improve user's satisfaction with skin care.

The light output device 2 may store the measured skin state in the memory 170 according to a period in which the user uses the light output device 2. The user may receive change in skin state according to information on the skin state stored in each period.

According to another aspect of the present invention, information on the measured skin state may be transmitted to the smartphone of the user.

According to the embodiment of the present invention, since skin care is performed according to the skin state of each part, skin care efficiency can increase.

Therefore, it is possible to improve user's satisfaction with skin care.

The present invention mentioned in the foregoing description can also be embodied as computer readable codes on a computer-readable recording medium. Examples of possible computer-readable mediums include HDD (Hard Disk Drive), SSD (Solid State Disk), SDD (Silicon Disk Drive), ROM, RAM, CD-ROM, a magnetic tape, a floppy disk, an optical data storage device, etc. The computer may include the controller 180 of the AI device.

What is claimed is:

1. A light output device for caring for a skin of a user using artificial intelligence, the light output device comprising:

a plurality of light sources configured to irradiate light;

a memory configured to store a skin care model learned using a deep learning algorithm to infer a facial skin state of the user;

a camera configured to capture an image of a face of the user; and a processor configured to:

acquire a skin state of each part of the face based on a first-type face image captured through the camera and the skin care model by classifying the first-type face image into a plurality of main parts and acquiring a plurality of first-type partial images respectively corresponding to the plurality of classified main parts, and converting the plurality of acquired first-type partial images into a plurality of second-type partial images and a plurality of third-type partial images, and control light output of the plurality of light sources based on the acquired skin state, wherein the light output is controlled by adjusting a light irradiation time and a light irradiation intensity of the plurality of light sources according to the acquired skin state of each part of the face.

2. The light output device of claim 1, wherein the first-type partial images correspond to an RGB type, the second-type partial images correspond to an infrared (IR) type and the third-type partial images correspond to an ultraviolet (UV) type.

3. The light output device of claim 2,
wherein the memory further stores an image conversion model for converting the first-type partial images into the second-type partial images and the third-type partial images, and
wherein the image conversion model is an artificial neural network based model learned using a deep learning algorithm or a machine learning algorithm.

4. The light output device of claim 3, wherein the image conversion model is composed of a convolutional neural network (CNN).

5. The light output device of claim 1, wherein the processor is further configured to determine the skin state from the plurality of second-type partial images and the plurality of third-type partial images using the skin care model.

6. The light output device of claim 5,
wherein the skin state comprises at least one of an amount of oil, a degree of wrinkles, an amount of moisture, a degree of elasticity, a degree of pigmentation or a degree of damage vulnerability of each part.

7. The light output device of claim 6,
wherein the processor is configured to determine a skin type of each part of the face based on the skin state,
wherein the skin type comprises a normal type and a damage type,
wherein the normal type comprises a dry type, an oily type, a normal skin type, a combination type, and
wherein the damage type comprises a serious pigmentation type and a serious damage vulnerability type.

8. The light output device of claim 7, wherein, when a degree of pigmentation is greater than or equal to a certain degree of pigmentation, the processor is further configured to determine that the skin type is the serious pigmentation type regardless of the normal type.

9. The light output device of claim 7, wherein, when a degree of damage vulnerability is greater than or equal to a certain degree of vulnerability, the processor is further configured to determine that the skin type is the serious pigmentation type regardless of the normal type.

10. The light output device of claim 7, wherein the processor is further configured to:
control light output of the plurality of light sources to perform a light output mode in a normal care mode based on a determination that the skin type is the normal type, and
control light output of the plurality of light sources to perform the light output mode in a concentrated care mode based on a determination that the skin type is the damage type.

11. The light output device of claim 1, further comprising a sound output unit;
wherein the processor is configured to output information on the acquired skin state through the sound output unit.

12. A method of operating a light output device for caring for a skin of a user using artificial intelligence, the method comprising:
capturing an image of a face of the user;
acquiring a skin state of each part of the face based on a skin care model learned using a captured first-type face image and a deep learning algorithm to infer a skin state of the face of the user by classifying the first-type face image into a plurality of main parts and acquiring a plurality of first-type partial images respectively corresponding to the plurality of classified main parts, and converting the plurality of acquired first-type partial images into a plurality of second-type partial images and a plurality of third-type partial images using an image conversion model; and
controlling light output of a plurality of light sources based on the acquired skin state, wherein the light output is controlled by adjusting a light irradiation time and a light irradiation intensity of the plurality of light sources according to the skin state of each part.

13. The method of claim 12,
wherein the first type is an RGB type, the second type is an infrared (IR) type and the third type is an ultraviolet (UV) type.

14. The method of claim 13,
wherein the image conversion model is an artificial neural network based model learned using a deep learning algorithm or a machine learning algorithm, and
wherein the image conversion model is composed of a convolutional neural network (CNN).

15. The method of claim 13, further comprising determining the skin state from the plurality of second-type partial images and the plurality of third-type partial images using the skin care model.

16. The method of claim 15, wherein the skin state comprises at least one of an amount of oil, a degree of wrinkles, an amount of moisture, a degree of elasticity, a degree of pigmentation or a degree of damage vulnerability of each part.

17. The method of claim 16, further comprising determining the skin type of each part of the face based on the skin type,
wherein the skin type comprises a normal type and a damage type,
wherein the normal type comprises a dry type, an oily type, a normal skin type, a combination type, and
wherein the damage type comprises a serious pigmentation type and a serious damage vulnerability type.

* * * * *